US00PP25302P3

(12) United States Plant Patent
Cavett

(10) Patent No.: US PP25,302 P3
(45) Date of Patent: Feb. 24, 2015

(54) ***ACER RUBRUM* NAMED 'JSC KINGSTWO'**

(50) Latin Name: *Acer rubrum*
Varietal Denomination: JSC Kingstwo

(76) Inventor: James David Cavett, Estill Springs, TN (US)

( * ) Notice: Subject to any disclaimer, the term of this patent is extended or adjusted under 35 U.S.C. 154(b) by 241 days.

(21) Appl. No.: 13/374,803

(22) Filed: Jan. 14, 2012

(65) Prior Publication Data

US 2013/0185834 P1 Jul. 18, 2013

(51) Int. Cl.
*A01H 5/00* (2006.01)

(52) U.S. Cl.
USPC ..... Plt./224

(58) Field of Classification Search
USPC ..... Plt./224
See application file for complete search history.

*Primary Examiner* — Kent L Bell
(74) *Attorney, Agent, or Firm* — Hornkohl Intellectual Property Law, PLLC; Jason L. Hornkohl

(57) ABSTRACT

A new and distinct *Acer rubrum* cultivar, named the 'JSC Kingstwo' maple is characterized by its variegated pigmentation of its leaves that varies with the age of the leaf; whereas, trees of *Acer rubrum* have no variegation known to the inventors. The 'JSC Kingstwo' maple is also characterized by its drought and cold tolerance.

7 Drawing Sheets

Figure 1:
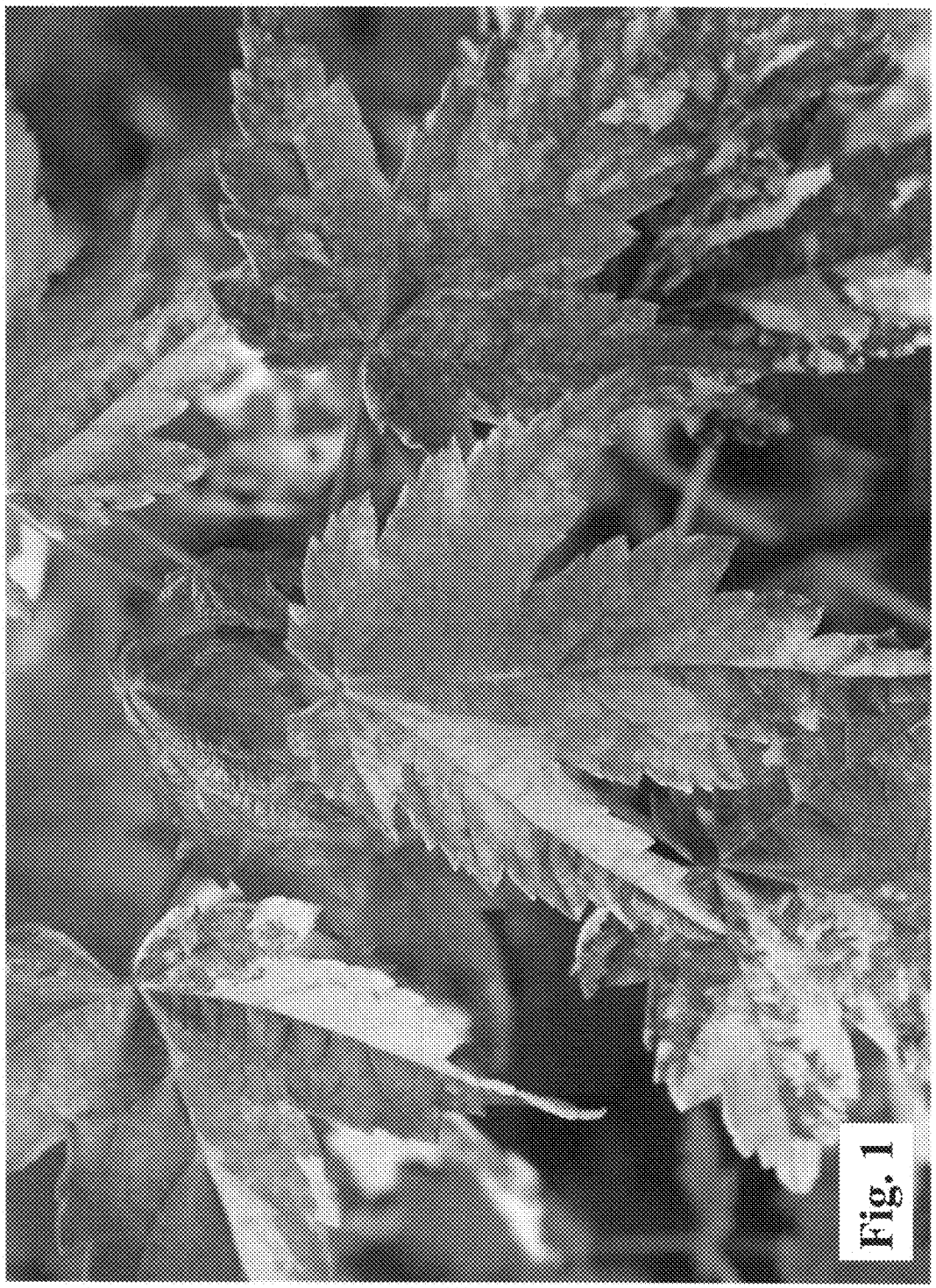

Latin name: *Acer rubrum.*
Varietal denomination: 'JSC Kingstwo'.

FIELD OF THE INVENTION

The present invention comprises a new and distinct cultivar of *Acer rubrum* and is referred to by the cultivar name 'JSC Kingstwo'.

BACKGROUND OF THE INVENTION

This new cultivar of *Acer rubrum*, the 'JSC Kingstwo' maple, was originally discovered as a naturally occurring limb mutation by James David Cavett in 2006 on one specific tree limb of an unnamed *Acer rubrum* tree planted in the yard of James D. Cavett at 74 S&W Lane, Estill Springs, Tenn. 37330. James D. Cavett took six cuttings off that single branch on the tree and rooted it in sand using Hormondin #3 (active ingredient is indole-3-butyric acid) at 74 S&W Lane, Estill Springs, Tenn. 37330 in July 2006. One of the 6 rooted cuttings survived. Sixty rooted cuttings were started from the 1 surviving rooted cutting in July 2007; these rooted cuttings were grown at 74 S&W Lane, Estill Springs, Tenn. Approximately 20 of the rooted cuttings begun in July 2007 survived and were used to begin 150 new rooted cuttings in July 2008 and 55 survived. In July 2009, approximately 250 rooted cuttings were taken and rooted in sand; approximately 125 rooted and survived. In July 2010, approximately 800 rooted cuttings were taken and rooted in sand; approximately 650 rooted and survived. In July 2011, approximately 2900 rooted cuttings were taken and rooted in sand; approximately 2000 rooted and survived. Over the last 5 years all the rooted cuttings of 'JSC Kingstwo' have exhibited the same growing characteristics and patterns as the parent tree, an unnamed *Acer rubrum*, except for the pigmentation of the leaves. The leaves of the rooted seedlings' pigmentation are reddish brown (172A-RHS) when the leaf breaks out of the bud. Within days of emerging from the bud, the reddish-brown color is surrounded by a light green (145A-RHS) pigmentation. As the leaf enlarges, portions of it become yellow (12A-RHS) until the large areas of the leaf become light yellow (8C-RHS) to whitish-yellow or cream (4D-RHS) color to white (N199D-RHS) mixed with green color (145A-RHS). Older growth leaves have speckles of cream (4D-RHS) on a dark-green background (137A-RHS). James D. Cavett has been evaluating these propagated seedlings for 5 years.

James D. Cavett is solely responsible for finding this new cultivar on his property, located at 74 S&W Lane, Estill Springs, Tenn. 37330. All propagation of this cultivar has been done by James D. Cavett at his nursery, located at 74 S&W Lane, Estill Springs, Tenn. 37330.

James D. Cavett immediately recognized that the new cultivar, 'JSC Kingstwo', exhibited new and distinctive leaf pigmentation. The leaves are reddish-brown when they first erupt from the bud. However, within days of emerging the leaf exhibits a mosaic of reddish-brown surrounded by a light green pigmentation. As the leaf enlarges and matures, the leaf pigmentation becomes whitish-yellow (cream) and a light green. The mature leaf exhibits cream color surrounded by dark green regions. All other growth characteristics of the cultivar are similar to the parent tree, an unnamed *Acer rubrum*. Only the seedlings that have originated from rooted cuttings of the original rooted stem that James D. Cavett rooted in 2006, exhibit the leaf pigmentation that is attributed to the new cultivar, 'JSC Kingstwo'. Over the last five years, only the rooted cuttings have exhibited this pigmentation as compared to other *Acer rubrum* trees known to the Inventor.

As shown in the first two photographs (a 2-year old seedling taken Jun. 22, 2008, labeled FIGS. 1 & 2) of the 'JSC Kingstwo' cultivar, the pigmentation of the leaves is distinctive and unique. The leaves that are coming out of the apical bud are reddish-brown in color. The young leaves immediately below the apical leaves retain this reddish-brown color for up to a week but the reddish-brown is quickly surrounded by a light green color as chlorophyll is produced. Leaves further down the stem, have a variegated yellow-green, green-yellow, and light green color. More mature leaves are also variegated (FIG. 3) and exhibit muted yellowish-green regions in a background of dark green and cream pigmentation. Because the cultivar and the parent tree that it came from are deciduous, the leaves turn color (from pink [56A RHS] to a purple-pink [68A RHS]). Other regions of the leaf exhibit a light yellow (15D RHS) color. The leaves drop off each fall in Zone 6b, which includes Middle Tennessee.

As shown in the third photograph (a 3-year old tree taken June 2009, labeled FIG. 3) of the 'JSC Kingstwo' cultivar, the pigmentation of the leaves is distinctive and unique. As the tree matures, not all leaves will exhibit the same degree of variegation. Some leaves show more variegation than others. For example, some will have more cream color than others. However, mature late summer leaves exhibit a variegated cream and light green mixture of pigmentation surrounded by a dark green pigmentation. The leaf has red petioles.

Figure 4:
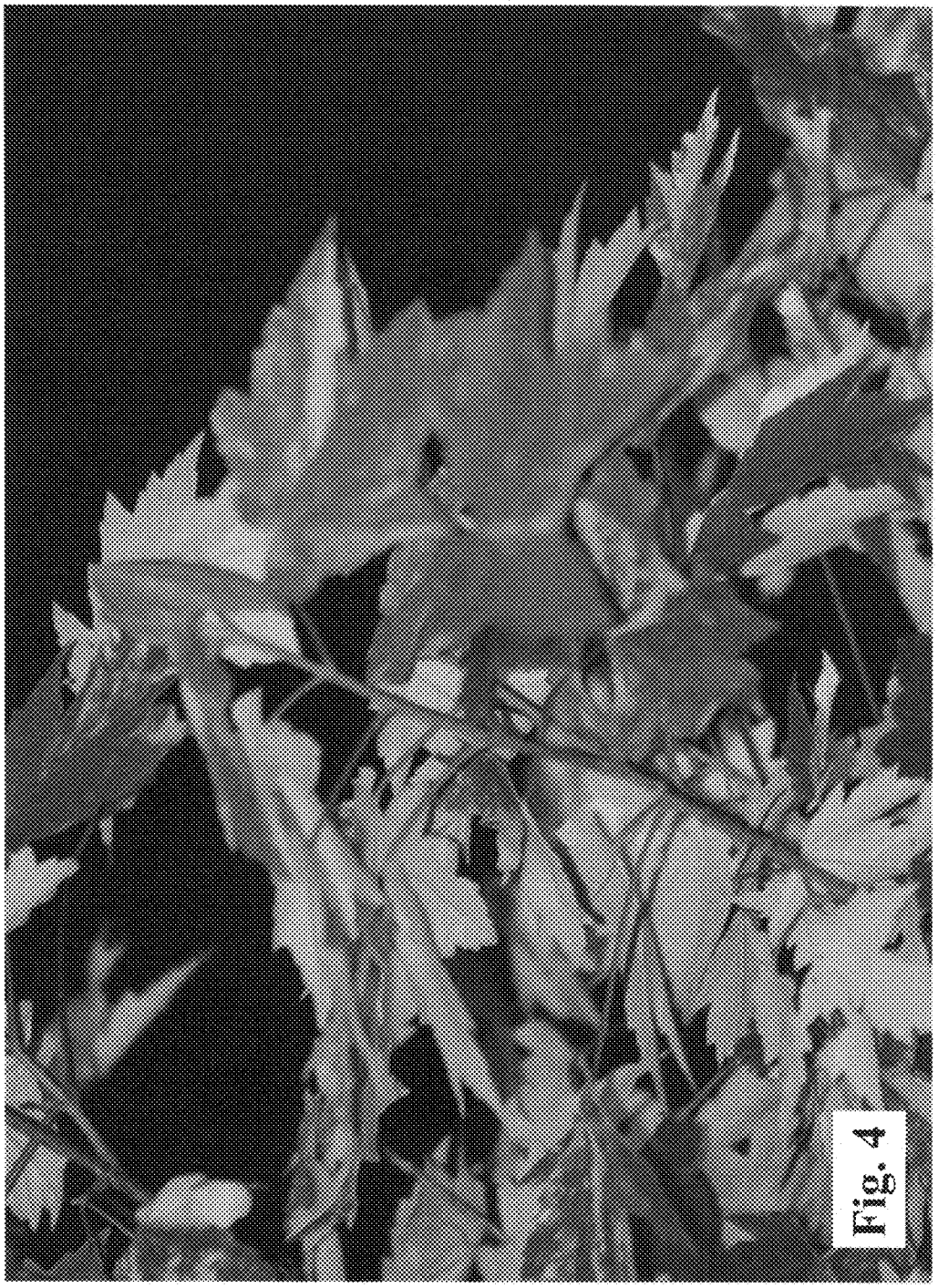

As seen in more detail (see FIG. 4), the seedling has an opposite arrangement. The leaves are 5 cm to 8 cm (or 2.0 to 3.1 inches) in length and 7.6 cm to 16.5 cm (or 3.0 to 6.5 inches) in width. The leaves consist of 3 to 5 shallow lobes with shallow tooth margins. The petioles are red (47A-RHS) when the leaf first opens and remain red. The red petioles persist into the fall as the leaves change color (see FIGS. 5 & 6). The diameter of petioles are ~0.3 to 0.4 cm and vary in length from 2 cm to 3.5 cm.

Figure 5:
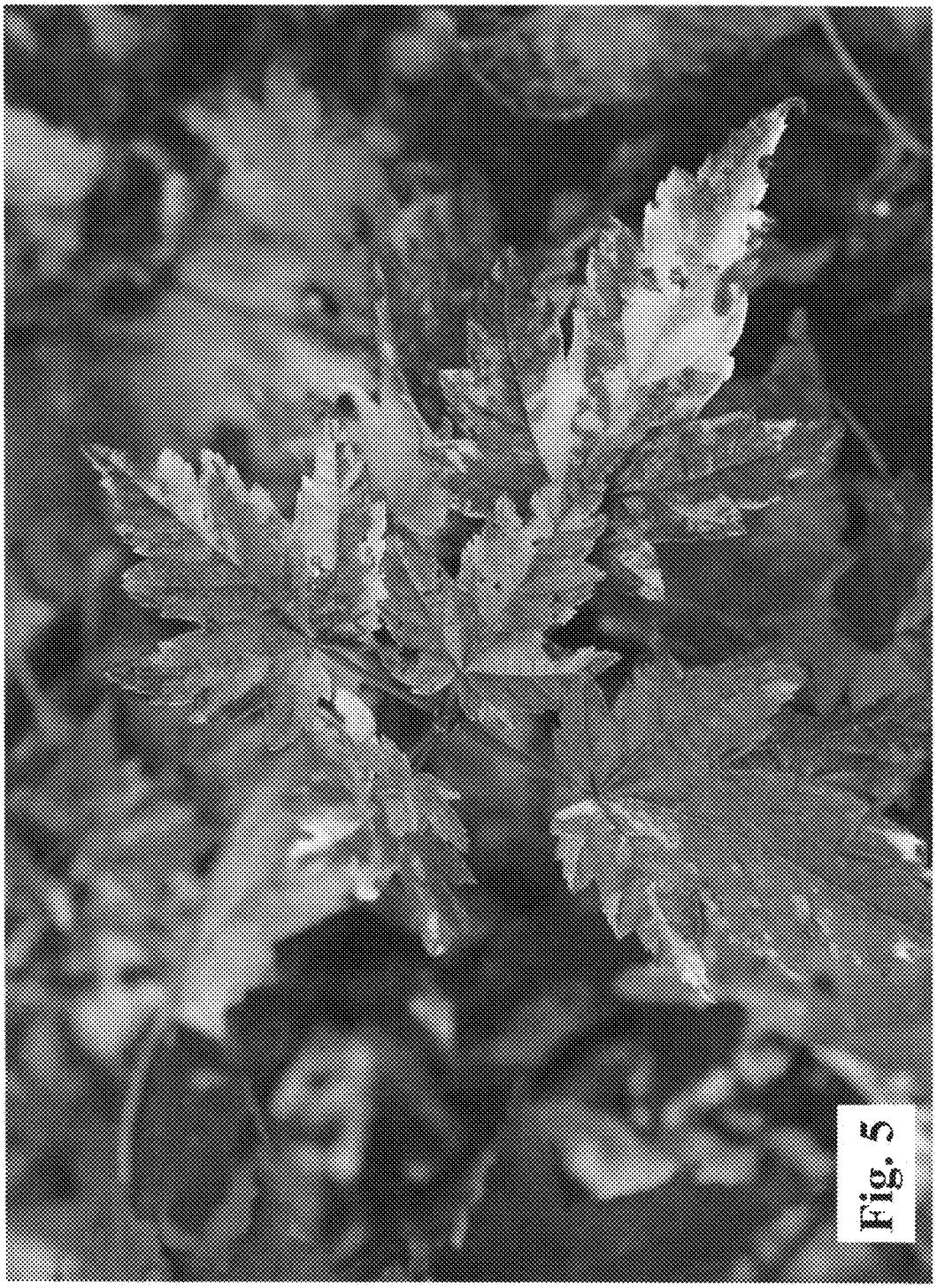
Figure 6:
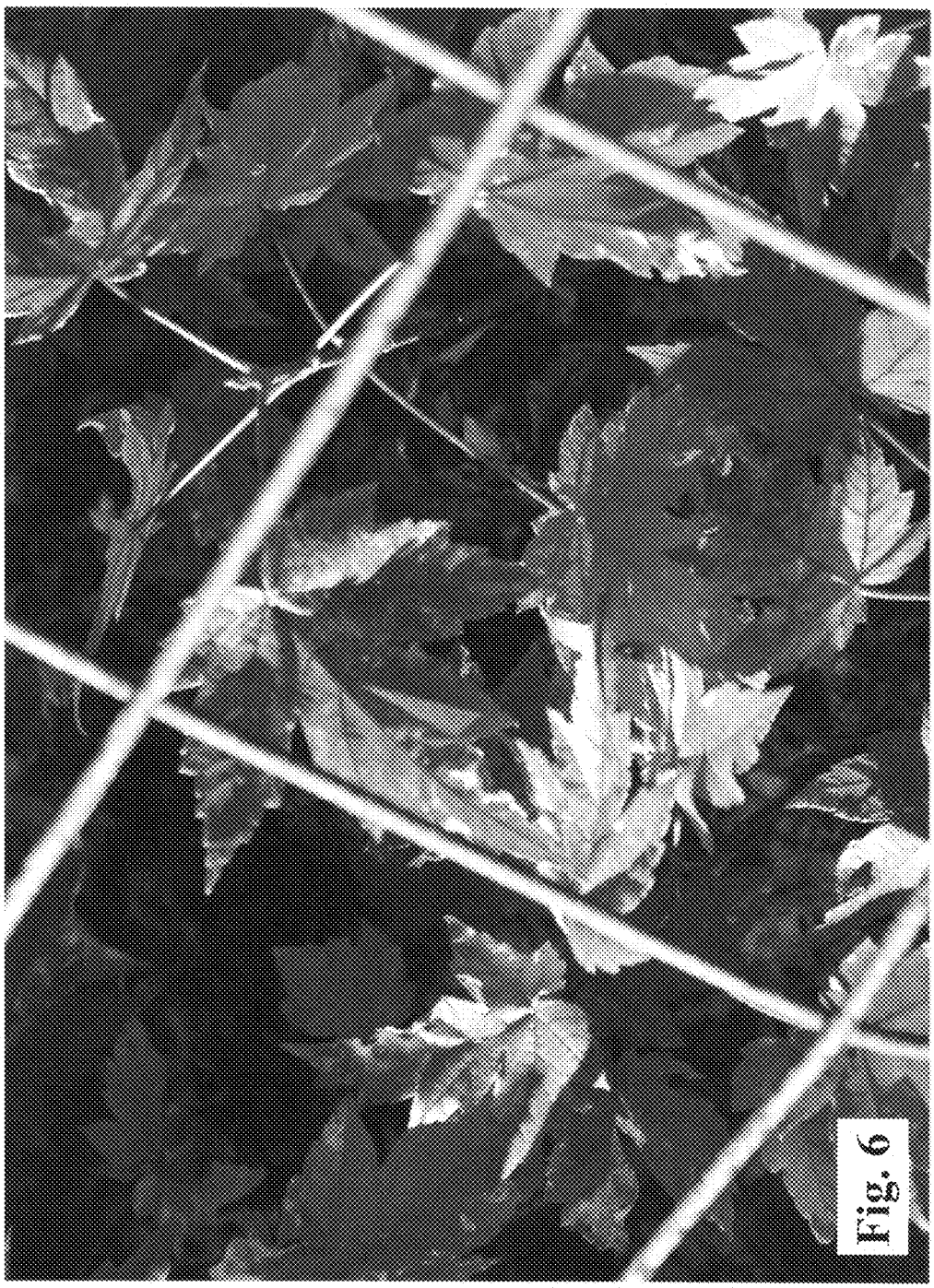

FIGS. 5 and 6 show the characteristic colors that the fall leaves take on. In early fall, the green chlorophyll begins to break down and is replaced by a light pink (56A-RHS) hue in the cream-colored portions of the leaf that spreads into the once green-pigmented regions giving it a purple-pink (68A-RHS) color (FIG. 5). By late fall, the leaf color becomes predominately red-brown (179B-RHS) with small areas of the leaf still exhibiting the light cream color that was first seen in the early spring several days after the leaf emerged for its bud. The petiole remains red (47A-RHS).

There are several flower buds at the end of each stem (see FIG. 7) that emerge in early spring (usually the end of February to early March in middle Tennessee) revealing sterile flowers that consist of 4 to 10 stamen that are yellow-green (145B-RHS) on yellow (23A-RHS) stalks. The flowers are encased in burgundy-red (45A-RHS) sepals before the flower emerges.

The 'JSC Kingstwo' cultivar has proven to be both drought resistant and winter hardy. From mid-May until mid-June 2011, Middle Tennessee (climate Zone 6b, USDA Plant Hardiness Zone Map) experienced an unusual spring drought and for the first two weeks of June 2011, Middle Tennessee experienced the hottest first two weeks recorded in Tennessee in June in decades. This was a particularly dangerous and damaging drought coupled with extreme heat because most of the trees had already budded. The 'JSC Kingstwo' cultivar survived this drought and extremely hot weather and continued to produce foliage throughout the spring and summer months. All rooted cuttings taken from the trees exhibit the same moderate growth that has been observed for the previous seasons that the 'JSC Kingstwo' cultivar has been cultivated.

The 'JSC Kingstwo' cultivar can also endure drastic changes in moisture. 'JSC Kingstwo' cultivar has been successfully grown without irrigation after it was moved into the fields during its third season. Each summer since it was rooted in 2006, it has endured the drought that Middle Tennessee has experienced during the months of July and August. However, this spring (2011) we had an unusual drought in Middle Tennessee between mid-May to mid-June. The cultivar survived this early spring drought without any irrigation.

The 'JSC Kingstwo' cultivar has been successfully propagated asexually. The proven means of asexual propagation has been rooted softwood cuttings. During the first year, the stem that was discovered by James D. Cavett was rooted as six cuttings in sand at his nursery at 74 S&W Lane, Estill Springs, Tenn. 37330; hence, only 6 cuttings were stuck in sand in 2006. In July 2007, 1 rooted cutting survived and was used to start 60 rooted cuttings in sand in July 2007 by James D. Cavett at his nursery. In July 2008, approximately 20 of 60 rooted cuttings that survived were used to begin 150 new rooted cuttings and 55 survived. In July 2009, 250 rooted cuttings were taken and rooted in sand; approximately 125 survived. In July 2010, 800 rooted cuttings were begun and approximately 650 survived. Approximately 2900 rooted cuttings were stuck in sand in July 2011 and 2000 survived. The cultivars have retained all the characteristics of the original selected seedling. It has been successfully propagated through 5 generations of asexual reproduction with a survival rate between 33% the second year (2007), 37% the third year (2008), 50% the fourth year (2009), and a 81% survival rate in the fifth year (2010). 69% of the cuttings have survived in 2011. Each generation has been stable and produced true-to-type trees each and every time the tree has been propagated.

The unique color of the leaves and moderate growth (3 to 6 feet per year) of 'JSC Kingstwo' cultivar make it well suited for a variety of landscaping uses. Furthermore, the 'JSC Kingstwo' cultivar is cold and drought tolerant. The cultivar is a moderate size tree whose leaf pigmentation is reddish-brown (172A-RHS) followed by a variegated light yellow (8C-RHS) to cream (4D-RHS) and white (N199D-RHS) surrounded by a light green (145A-RHS) color in the weeks following their emergence from the bud. The mature leaf exhibits a variegated cream (4D-RHS) with a splash of light yellow (8C-RHS) and dark-green (137A-RHS) color. In the fall, the leaves turn from a variegated cream on a green background to a purple-pink (68A-RHS) mixture consisting of reds and pinks with a light yellow (12A-RHS) in the creamy variegated portion of the leaf (see FIG. 5) until the green pigmentation is replaced by the pink and purple-pink (68A-RHS) color interspersed with the variegated light cream color (see FIG. 6). The unique color of the leaves of the 'JSC Kingstwo' cultivar will make it a popular maple tree for those who desire attractive coloration from early spring through the fall.

SUMMARY OF THE INVENTION

The following characteristics in combination distinguish the new tree named 'JSC Kingstwo' cultivar from other cultivars of *Acer rubrum* known to the Inventor.

1. The 'JSC Kingstwo' cultivar has a distinctive and unique variegated leaf that the parent tree, an unnamed *Acer rubrum*, and other cultivars of *Acer rubrum* known to the Inventor do not have. The colors of the leaves change throughout the growing season. The entire leaf is a reddish-brown when it first emerges from its bud. Within a couple of days the leaf color is a mixture of this same reddish-brown color with a light green color. However, within two weeks, the reddish-brown pigmentation disappears and large areas of the leaf become variegated, culminating with a variegated light yellow color mixed with cream and dark green or white and dark green pattern in the mature leaf in late summer/early fall. The cream and white regions found in the mature leaf in the summer are initially replaced with different hues of pink color and green regions of the summer leaf are replaced by a resplendent purple-pink in the fall.

2. With the distinctive, variegated foliage colors that change throughout the growing season, the 'JSC Kingstwo' cultivar will be a popular tree for landscaping applications. While it doesn't grow as quickly as other *Acer rubum* cultivars, it has a larger crown and more limbs, and the leaves are not as deeply lobed.

3. The 'JSC Kingstwo' cultivar is cold tolerant, easily surviving the temperatures experienced in Middle Tennessee (climate Zone 6b, USDA Plant Hardiness Zone Map).

4. The 'JSC Kingstwo' cultivar is able to endure drastic changes in moisture levels. There is usually heavy rainfall in the spring and very little rain in July, August, and September in Middle Tennessee (climate Zone 6b, USDA Plant Hardiness Zone Map). During the past 5 years this cultivar has survived some severe drought conditions. In 2007, there was little rain in the spring and late summer. In 2011, there was an unusual two-week long, early spring drought that coincided with the hottest temperatures for several weeks on record in Middle Tennessee for many decades. Yet, the cultivar thrived. In summary, the 'JSC Kingstwo' cultivar has survived annual summer droughts, including the severe drought during the summer of 2007 and endured record high temperatures during these drought conditions.

5. The 'JSC Kingstwo' cultivar grows at a moderate rate. The seedlings grew 3 to 4 feet during their first year and 5 to 6 feet during their second year. During their third year, their average trunk size measured 4.38 cm or 1.7 inches.

6. After 5 years of growth, the 'JSC Kingstwo' cultivar has remained insect and pathogen resistant, growing in the fields of Middle Tennessee.

7. The 'JSC Kingstwo' cultivar has not been observed under all conditions, and it is not known how the cultivar might respond to various conditions.

BRIEF DESCRIPTION OF THE PHOTOGRAPHS

The first photograph (FIG. 1) shows the red-brown (172A-RHS) leaves as they emerge from the apical leaf bud and the yellow-green and cream-green variegated leaves as one moves from the top of the seedling to the base of the tree. All leaf petioles are red (47A-RHS). This seedling is the one surviving seedling that James D. Cavett rooted in July 2006 at 74 S&W Lane, Estill Springs, Tenn. 37330.

Figure 2:
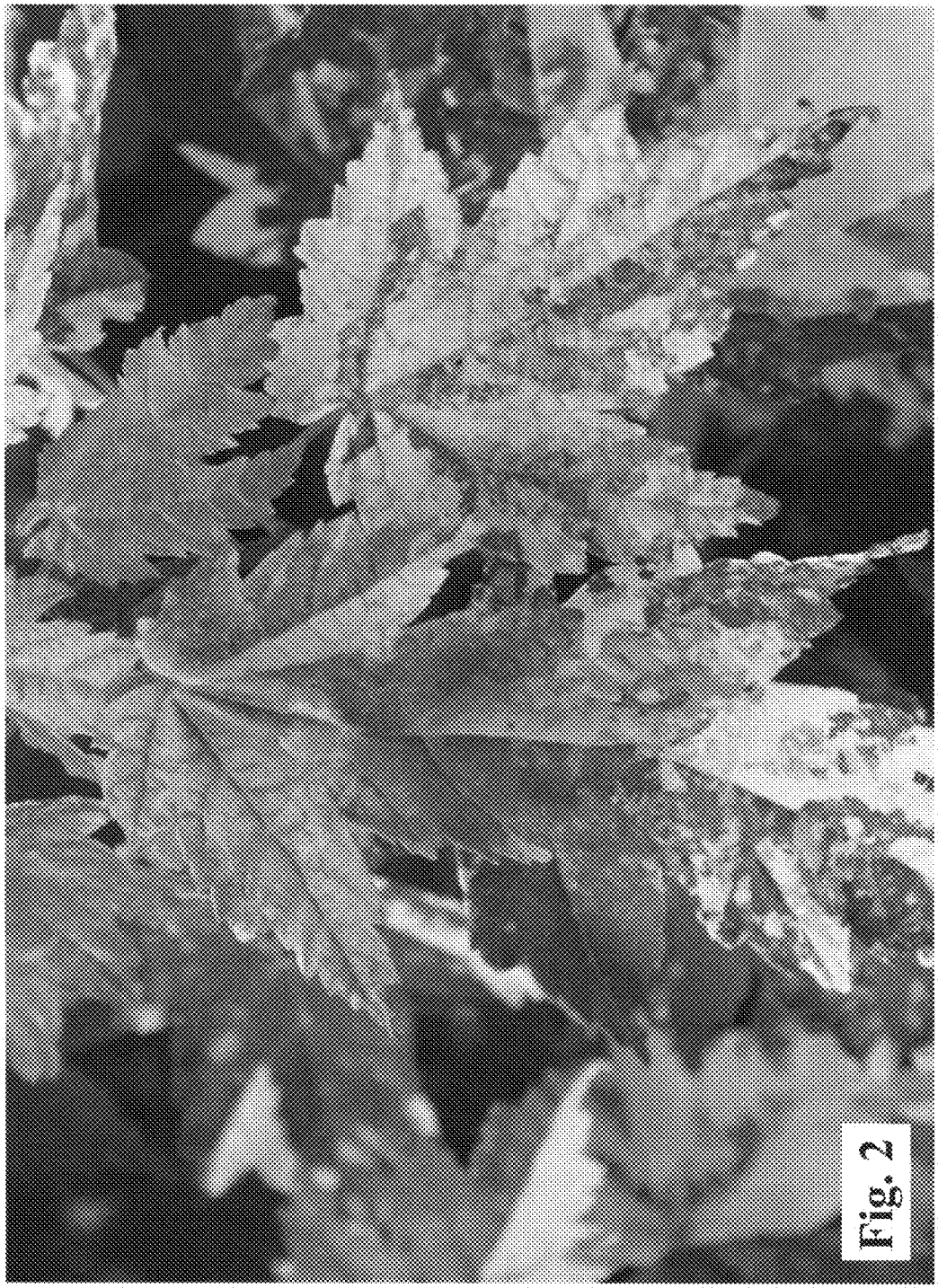
Figure 3:
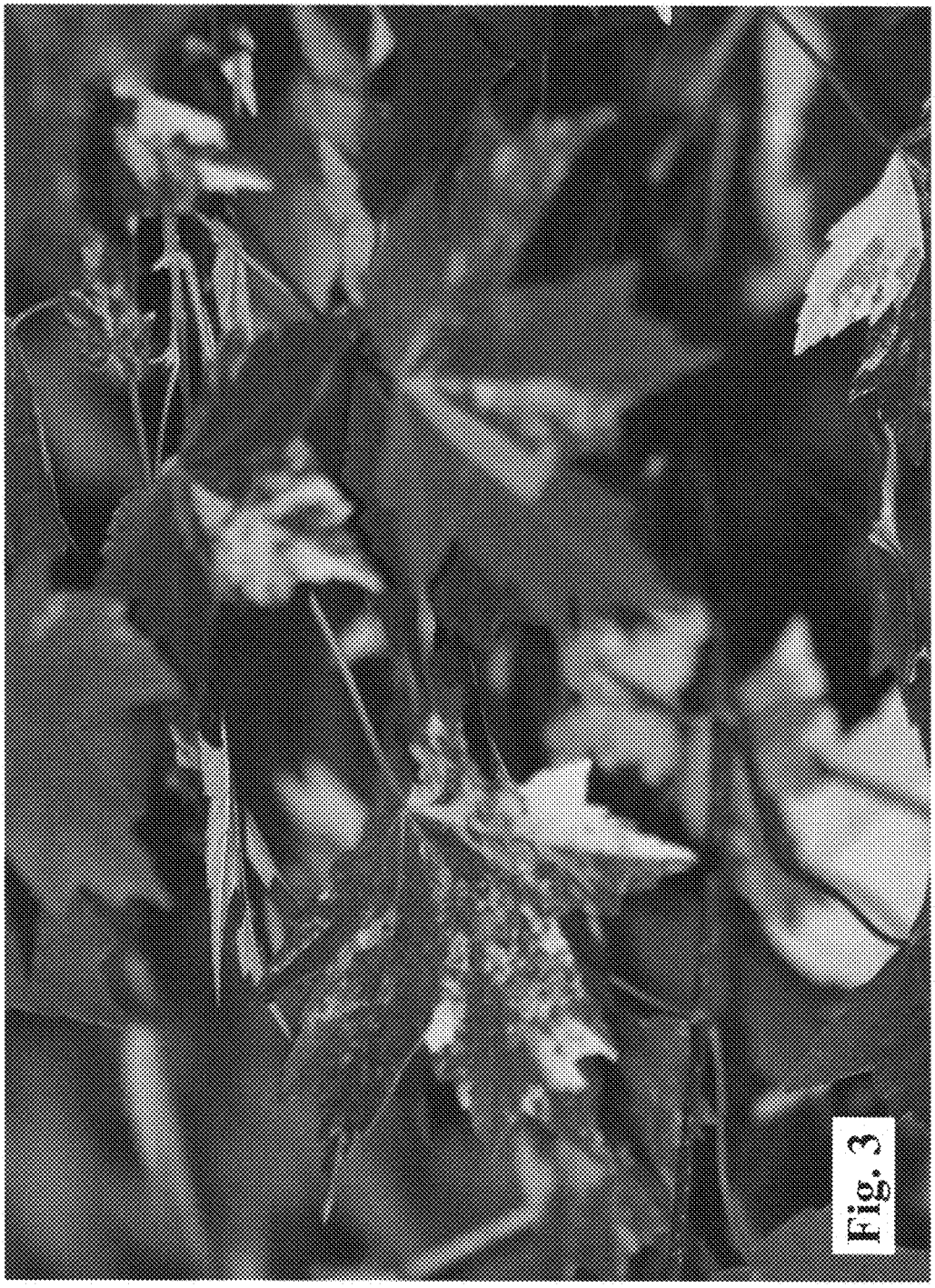

FIG. 2 shows the originally discovered 'JSC Kingstwo' as it looked in 2008, two years after its discovery at 74 S&W Lane, Estill Springs, Tenn. 37330. This photograph shows the color of the leaves a couple of weeks after the leaf emerges from its bud. Notice that the leaves are variegated and have a large area of light green color around the major veins. The color along the leaf margin varies from light green (145A-RHS) mixed with a light yellow (8C-RHS) or cream (41D-RHS) color.

The third photograph (FIG. 3) shows the color of mature leaves. It exhibits a very similar variegation to the younger leaf seen in FIG. 2 except that the green is much darker (137A-RHS). Notice that the petiole remains red (47A-RHS) in the more mature leaf.

The fourth photograph (FIG. 4) shows the apex of a seedling. The leaf that emerged from the apical meristem is the reddish-brown (172A-RHS) with regions of green (145A-RHS). The stunning variegation pattern of the leaf pigments is seen in all the leaves in this photograph. From the apex as one moves down the branch, the yellow and cream color is mixed with large portions of green pigmentation. Notice that the green pigmentation is darker on leaves that are further from the apex of the branch as described in FIG. 3. The opposite arrangement of the leaves on the branch is apparent in this photograph.

The next photograph (FIG. 5) shows early fall leaf colors. In this photograph, we see that the regions of the leaf that were predominately cream or yellow in color are the first to turn a pink (56A-RHS) to purple-pink (68A-RHS) color as the fall colors develop. There is also a hint of pink to red color developing in the green-pigmented portions of the leaf as the chlorophyll begins to break down.

The sixth photograph (FIG. 6) shows late fall leaf colors. Late in the fall, more of the leaf develops the pink-purple color that is seen as the leaf begins to develop fall colors (see FIG. 5). Most of the leaf develops a deep red-brown (179A-RHS) color as the chlorophyll continues to break down until the entire leaf is red.

Figure 7:
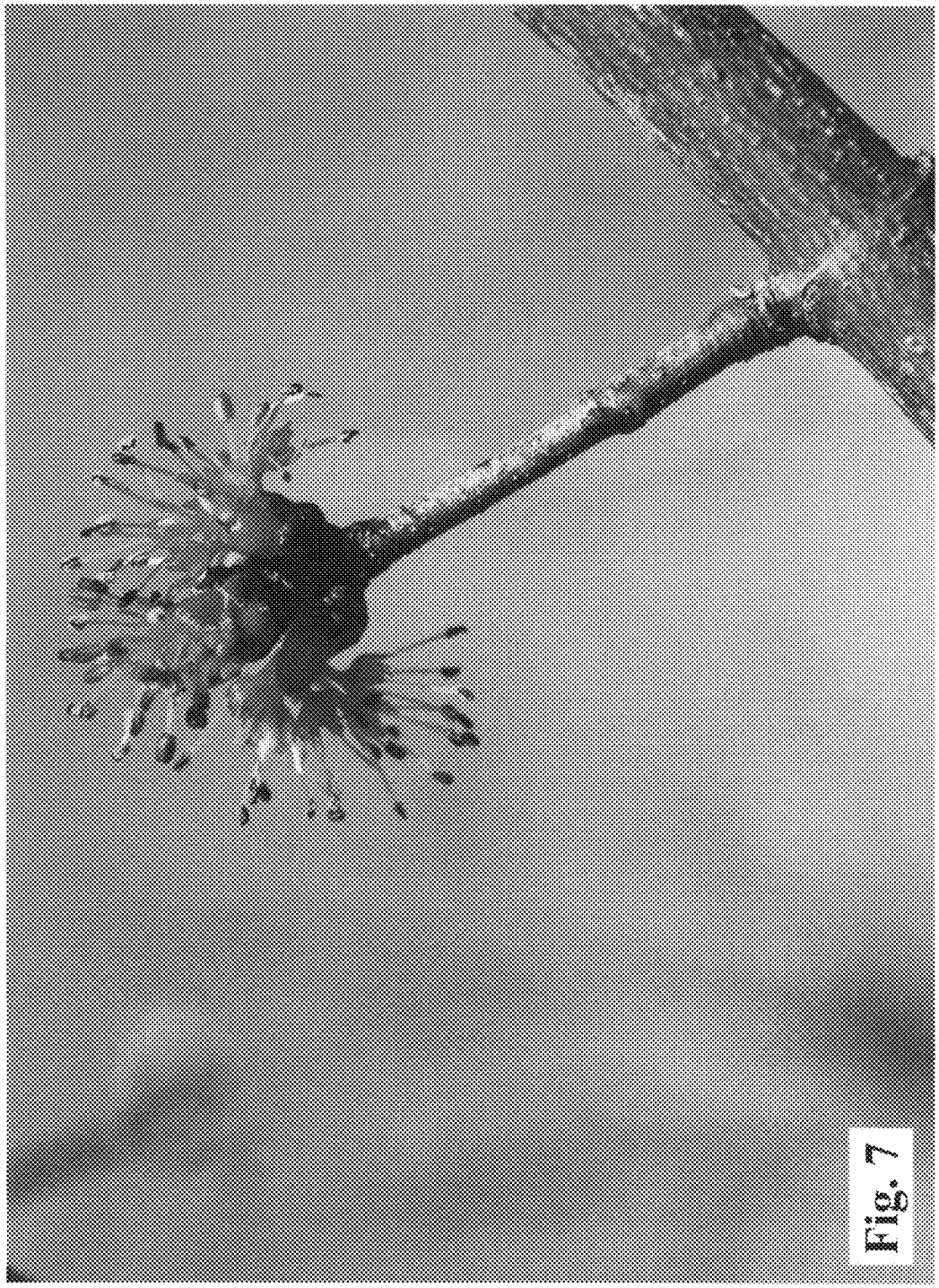

In FIG. 7, one sees the flowers that emerged in March 2011 on the 'JSC Kingstwo' seedling. Multiple flowers emerge from the flower bud in early spring. The flowers consist of 4 to 10 yellow-green (145B-RHS) stamen supported on a yellow stalk (23A-RHS) over the ovary.

DETAILED BOTANICAL DESCRIPTION

The following observations, measurements, and values describe trees grown at 74 S&W Lane, Estill Springs, Tenn. 37330. The actual appearance and characteristics of any individual tree will vary due to horticultural practices and local conditions. The tree used in the description is 4 years old. Color references are made to The Royal Horticultural Society Colour Chart except where terms of ordinary significance are used.

Botanical classification: *Acer rubrum.*

Commercial classification: 'JSC Kingstwo' maple.

Origin: One specific branch that had variegated loaf colors was cut from the parental tree, an unnamed *Acer rubrum*. This specific branch was the sole branch on the tree that exhibited variegation and from this branch the six cuttings were taken and rooted.

Parentage: The unnamed *Acer rubrum* tree from which the mutated limb was obtained.

Propagation: Asexual by softwood cuttings that were rooted in sand.

Plant:

*Growth rate.*—Moderate; an average of 3 to 6 feet per year or 91 to 183 cm.

*Form.*—Oval.

*Shape.*—Oval to round.

*Height.*—Average size of the 'JSC Kingstwo' is 30 to 35 feet or 914 to 1067 cm.

*Spread.*—Average size of the 'JSC Kingstwo' is 15 to 20 feet or 457 to 610 cm.

*Density.*—Thick with foliage.

*Trunk size.*—2.0 to 3.0 inches or 5.0 to 7.6 cm diameter at the base of the trunk at ground level after 5 years. The color of the bark on the trunk of a 5-year-old tree varies from N200C-RHS to N202C-RHS.

*Bark.*—(Trunk): Smooth, color is (N199C-RHS) textured with tiny raised lenticels.

*Branching arrangement.*—Opposite. Angle of attachment: Ranges from 45 to 90 degrees with 45 to 60 degrees being most prevalent. Internodal length: Mature branches range from 3.8 to 5.0 cm or 1.5 to 2.0 inches on a 1-year-old seedling. The average length of a typical branch is 4 to 5 feet or 122 to 152 cm, and the average diameter of a typical branch is 1.0 to 2.0 inches or 2.5 to 5.0 cm in diameter, on a 5-year-old tree.

*Stem*.—The color of the mature stems is gray (199A-RHS). On the new growth, the stem color is a mixture of two colors. The youngest portion of the stem is reddish-brown (172A-RHS) and the older portion of the stem is purple-brown in color (166A-RHS). The average stem length is 122 to 152 cm or 4 to 5 feet; the average stem diameter is from 0.4 to 0.5 cm or 1.0 to 1.3 inches. The arrangement of leaves is opposite. The length of new growth stem on a 5-year-old seeding ranges 30.5 to 76.2 cm or 12 to 30 inches with a diameter of 0.4 to 0.5 cm or 1.0 to 1.3 inches. The internodal length on the 5-year-old tree varies from 4.0 to 9.0 cm or 1.6 to 3.5 inches and average 6.5 cm or 3.9 inches.

*Lenticels*.—Small, but conspicuous, silver in color. They are 0.5 to 1.0 mm in length and 0.1 to 0.5 mm in width. The color of the lenticels is 202C-RHS.

*Leaves*.—Deciduous.

*Leaf length*.—Petioles vary from 3.5 cm to 9.0 cm or 1.4 to 3.5 inches on young leaves found at the apex of the limb, but average 6.0 cm. Leaf length of the blade varies from 5.0 cm to 8.0 cm or 2.0 to 3.1 inches in length and the width of the leaf varies from 7.6 cm to 16.5 cm or 3.0 to 6.5 inches. The color of the petiole is red (47A-RHS) when the leaf first opens but the mature petiole is dark purple to red (53A-RHS) in color and has an average diameter of 0.04 inches or 0.1 cm.

*Average leaf width*.—4.0 cm or 1.6 inches on growing branch tips (near the apical meristem) and 8.0 cm or 3.1 inches at the base of the branch.

*Leaf shape*.—Lobed with 3 or 5 shallow lobes.

*Leaf margin*.—Tooth.

*Leaf texture*.—Smooth on the upper and lower surfaces of the leaf, the lower surface has some hairs and the color is lighter on the upper side of the leaf than the lower side.

*Leaf quantity*.—Abundant.

*Leaf color*.—When the leaves first emerge from the bud, they are red (41A-RHS) to reddish brown (172A-RHS) in color. The red of the newly emergent leaf is quickly muted by the green of the chlorophyll that is forming. Several weeks after emerging from the bud, the leaf color becomes variegated and contains a light yellow (8C-RHS) mixed with light green (145A-RHS). The upper side of new growth (3-week-old leaves): the 3-week-old leaves have a mixture of reddish-brown (172A-RHS) and yellow-brown (163A-RHS); the upper side of the most mature leaves have a mixture of dark green (137A-RHS) and light yellow (15D-RHS) or yellow-green (145A-RHS). Lower side of the leaf: the color mixture is similar to the upper side at early leaf ages, but changes in the most mature leaves to a mixture of green (194A-RHS) and light yellow (8C-RHS) or whitish-yellow (4D-RHS).

*Leaf ribs and veins*.—The upper rib surface at the petiole end of the leaf is dark pink-red (53C-RHS) to greenish-white (146C-RHS) at the tip of the leaf. The lower rib surface (leaf underside) color is dark pink-red (53C-RHS) at the petiole end of leaf and yellow-green (145B-RHS) at the tip of the leaf. Venation is netted.

*Vegetative buds*.—Terminal bud or apical bud is red (45A-RHS) before the leaf emerges from the bud. Lateral buds are conical and 0.12 to 0.4 inches or 3 to 4 mm in length and red in color (45A-RHS).

*Leaf apex*.—The leaf apex is acute.

*Base descriptor*.—Rounded.

Flowers: Seedless but produces flowers. Flowers appeared in early March 2011. There were 3 to 4 flower buds at each node (FIG. 7). There were 4 to 10 stamen (FIG. 7) in each flower and were yellow-green (145B-RHS). The stalk of the stamen is yellow (23A-RHS). The inflorescence typically is 15 to 20 mm from the base of the peduncle to the tip of the anther, and 3 to 5 mm in diameter from petal to petal. Due to the sterile nature of this specimen, the flowers do not have pistils, and therefore no ovaries or stigma, and the flowers do not pollenate.

Petals: 6-8 petals on each flower, the petals are 3 to 5 mm in length and 1 to 2 mm in diameter. Ovular in shape with a smooth texture both inside and out. The apex on the petals in acute with a tooth margin. The outside color of the petals is orange-red (39B-RHS), and the inside color of the petals is a light pink (65B-RHS).

Sepals: The sepals are 3 to 5 mm in both length and diameter. There are hexagonal in shape with a smooth texture on both inside and out. The apex of the sepals is acute with a tooth margin. The color both inside and out is dark pink red (53C-RHS).

Flower buds: The buds of the flowers are circular in shape. They are 4 to 6 mm in diameter and 3 to 8 mm in length.

Peduncles: The peduncles are 1 to 4 mm in length and 0.2 to 0.5 mm in diameter. The peduncles are an orange red (31D-RHS).

Anther: The anther length is 0.5 mm to 1 mm in length, and are yellow-green (145A-RHS) as the flower emerges from the bud, and eventually turns a dark green (137A-RHS) as the flower matures.

Disease and pest resistance: No known susceptibility to diseases or pests common to *Acer rubrum*.

What is claimed:

1. A new and distinct cultivar of *Acer rubrum* tree named 'JSC Kingstwo' as illustrated and described herein.

* * * * *